United States Patent [19]

Lezdey et al.

[11] Patent Number: 5,215,965
[45] Date of Patent: * Jun. 1, 1993

[54] TREATMENT OF INFLAMMATION

[76] Inventors: John Lezdey, 976 Kingston Dr., Cherry Hill, N.J. 08034; Allan J. Wachter, 9822 S. Grandview, Tempe, Ariz. 85284

[*] Notice: The portion of the term of this patent subsequent to Mar. 2, 2010 has been disclaimed.

[21] Appl. No.: 755,300

[22] Filed: Sep. 5, 1991

Related U.S. Application Data

[63] Continuation-in-part of Ser. No. 591,752, Oct. 2, 1990, Pat. No. 5,093,316.

[51] Int. Cl.$^5$ .................. A61K 37/64; A61K 31/57
[52] U.S. Cl. ........................................ 514/12; 514/8; 514/21
[58] Field of Search ............... 514/8, 12, 21; 530/380, 530/395

[56] References Cited

PUBLICATIONS

Watorek et al Neutrophils Elastase & Cathepsin G (1988) vol. 240 pp. 23-44.
Hargreave et al Eur. J. Respir. Dis (1986) (Suppl. 147) pp. 16-21.
Holgate et al Clinical Allergy, (1985) vol. 15 pp. 221-234.
Wasserman Annals of Allergy (1989) vol. 63 No. 6 Pt Supp.
Pipkorn et al J. Clin. Invest., vol. 80 Oct. 1987, pp. 957-961.
Clinical Investigation—JAMA, Sep. 2, 1988—vol. 260. #9.
Insight In Allergy—vol. 5, No. 1, Apr. 1990.

*Primary Examiner*—Michael G. Wityshyn
*Assistant Examiner*—Choon P. Koh
*Attorney, Agent, or Firm*—John Lezdey

[57] ABSTRACT

A method for the prophylaxis or direct treatment of mast cell implicated pulmonary diseases which comprises administering an effective amount of a corticosteroid and at least one serine protease inhibitor, its salts, derivatives or analogs which bind with the mediators of mast cells or T-cells.

10 Claims, No Drawings

TREATMENT OF INFLAMMATION

RELATED APPLICATIONS

This application is a continuation-in-part of application Ser. No. 591,752 filed Oct. 2, 1990, now U.S. Pat. No. 5,093,316 of Lezdey et al entitled "Treatment of Inflammation."

FIELD OF THE INVENTION

The present invention relates to a method and composition for treating mammals afflicted with pulmonary mast cell implicated disease. More particularly, the present invention relates to the direct or prophylaxis treatment of certain pulmonary mast cell implicated diseases, by administering serine protease inhibitors, their analogs, salts or derivatives in combination with corticosteroids whereby a synergistic effect is found. There is particularly provided compositions for treating asthma by inhalation therapy and for related sinusitis.

BACKGROUND OF THE INVENTION

Prior to the present invention it was generally believed that serine protease inhibitors could be used only to supplement a deficiency occurring as a result of a genetic defect or a chemically produced deficiency resulting from an event such as smoking. Moreover, no consideration was previously given for directly controlling diseases in which mast cells are implicated by administering serine protease inhibitors when serum levels of proteases or protease inhibitors are normal. Mast cells have been found to be implicated in diseases and events such as allergic and non-allergic rhinitis, nasal polyposis, atopic dermatitis, psoriasis, contact dermatitis, pancreatitis, emphysema, asthma, colitis, Crohn's Disease, wound healing, cluster headaches, coronary artery spasm, rheumatoid arthritis etc.

Inflammation is a non-specific response of tissues to diverse stimuli or insults and results in release of a variety of materials at the site of inflammation that induces pain. It is now recognized that mast cells are implicated in the pathophysiology of inflammatory skin conditions as well as in other physiological disorders. Mast cells provide the greatest source of histamines in acute inflammation.

Neutrophils are a source of serine elastase and cathepsin G which are important in the tissue damage of inflammation, especially in cystic fibrosis.

The most direct approach to therapy of inflammatory conditions appears to be a direct attack at the site of inflammation of the mediators of inflammation and pain and the reduction of those neutrophilic derivatives which can cause damage to existing tissue and to the growth of new tissue.

Alpha 1-antichymotrypsin is a plasma protease inhibitor synthesized in the liver. It is a single glycopeptide chain of approximately 68,000 daltons and belongs to a class of serine protease inhibitors with an apparent affinity toward chymotrypsin-like enzymes.

Alpha 2-macroglobulin is a glycoprotein containing 8-11% carbohydrate which can be isolated from plasma by gel filtration chromatography.

Alpha 1-proteinase inhibitor (alpha 1-antitrypsin) is a glycoprotein having a molecular weight of 53,000 determined by sedimentation equilibrium centrifugation. The glycoprotein consists of a single polypeptide chain to which several oligosaccharide units are covalently bonded. Human alpha 1-proteinase inhibitor has a role in controlling tissue destruction by endogenous serine proteinases. A genetic deficiency of alpha-1-proteinase inhibitor, which accounts for 90% of the trypsin inhibitory capacity in blood plasma, has been shown to be associated with the premature development of pulmonary emphysema. The degradation of elastin associated with emphysema probably results from a local imbalance of elastolytic enzymes and the naturally occurring tissue and plasma proteinase inhibitors. Alpha-1-proteinase inhibitor inhibits human pancreatic and leukocyte elastases. See Pannell et al, Biochemistry. 13, 5339 (1974); Johnson et al, Biochem. Biophys. Res. Commun., 72 33 (1976); Del Mar et al, Biochem. Biophys. Res. Commun., 88, 346 (1979); and Heimburger et al, Proc. Int. Res. Conf. Proteinase Inhibitors. 1st, 1-21 (1970).

C-reactive protein (CRP) has been reported by Mold et al in J. Exp. Med. 154, 1,703-1,708, 1,984, of protecting mice exposed to *S. pneumonia*.

The article of Groutas entitled "Inhibitors of Leukocyte Elastase and Leukocyte Cathepsin G Agents for the Treatment of Emphysema and Related Ailments" medical Research Reviews, Vol. 7, No. 7, 227-241 (1987), discloses the role of eglin, elastinal 1 and elastin in emphysema.

McElvaney et al in *Lancet,* Vol. 337, p. 337, p. 392-394, Feb. 16, 1991, which is incorporated herein by references, discloses aerosol α1-antitrypsin treatment for cystic fibrosis.

U.S. Pat. No. 4,732,973 to Barr et al discloses typical analogs of serine protease inhibitors which may be used in the present invention.

U.S. Patent No. 4,916,117 to Lezdey et al discloses the treatment of pulmonary inflammation with microcrystalline alpha-1-antichymotrypsin.

It is understood that the term "serine protease inhibitors" as used herein refers to the inhibitors derived from a particular species and inhibits the proteases of the same species. However, human serine protease inhibitors may be used in veterinary products but not visa versa.

SUMMARY OF THE INVENTION

The present invention relates to a method for treating pulmonary inflammatory conditions in patients with mast cell implicated diseases by the administration of a corticosteroid and a serine protease inhibitor, its analogs, salts or derivatives, alone or in combination with one or more other serine protease inhibitors which have a specific activity for mast cells or the proteases derived therefrom such as cathepsin-G, elastase, human mast cell chymase, kinins, basophils, and T-cell proteases or their precursors in a suitable pharmaceutical composition.

A cocktail or mixture of serine protease inhibitors would therefore be useful to deactivate those mediators of inflammation which may not yet be recognized but are found in association with a particular inflammatory disease.

It has now been found that in certain pulmonary diseases, neutrophils, mast cells, T-cells and their mediators induce an inflammatory state resulting in a localized imbalance of elevated serine protease with a concomitant deficiency of their naturally occurring inhibitors despite normal serine protease inhibitor serum levels. Mast cells are critical in recruiting the cells (eosinophils, basophils and neutrophils) involved in the late phase reaction (LPR). Mast cell and neutrophil mediators appear to have a central role in the LPR. Monocytes through the release of cytokines, interleukin -1,6 and tumor necroses factor further amplify the LPR. Platelet activating factor, a mediator from mast cells, neutrophils and platelets is a potent bronchoconstrictor. Histamines are also released by the degranulation of mast cells as well as leukotriene T4 (LTB4) which play an important role in asthma. IgE upon activation by an antagonist causes degranulation of mast cells. Alpha 1-antitrypsin, as well as alpha 1-antichymotrypsin inhibits the mediators of mast cells and neutrophils, and also regulates IgE biosynthesis. The T-cell lymphokine glycosylation enhancing factor (GEF) is a serine protease that has been shown to enhance IgE response. By also inhibiting GEF with alpha 1-antitrypsin there is a two level inhibition in the inflammatory cascade. The serine protease inhibitors decrease mast cell mediator release by inhibiting local IgE biosynthesis and T-cell lymphokine production. Serine proteases not only activate kinins and complements but also mediate tissue necrosis. The serine proteases, elastase and cathepsin G, have been shown to stimulate the production of platelet activating factor and LTB4.

Alpha 1-antichymotrypsin is important because it binds with basophils which have a high content of cathepsin G. By controlling the basophils there is also control of the histamine release factor.

With the combination of alpha 1-antichymotrypsin and alpha 1-antitrypsin there is a control of the activation of IgE by GEF and a control of basophils. With the combination together with a corticosteroid there is a control of IL-1. Consequently, a complete turn-off of inflammation occurs.

The serine protease inhibitor may be administered alone or in combination with a corticosteroid in an aerosol generating system wherein the drugs are aerosolized using a compressed air driven nebulizer selected on the basis of its ability to generate an aerosol with microcrystalline particles or droplets of optimal size (<3 mm aerodynamic diameter). To generate the aerosol containing serine protease inhibitor and corticosteroid for example about 2 mL of inhibitor and about 2 mL of corticosteroid at a concentration of both being about 25 mg/mL is placed in the reservoir of the nebulizer driven by compressed air.

Depending upon the disease and the severity of the disease, it is possible to treat by aerosolization of 1.5 mg/kg of inhibitor every 12 hours for one week with combined or single administration of corticosteroid.

Where the disease treated is asthma, the composition should be non-aqueous and the particles less than 3 microns.

CRP is believed to provide a beneficial effect in combination with other inhibitors because it binds with the calcium ions present in cases such as cystic fibrosis to complex with polysaccharide moieties which are antibacterial and further to bind with complements.

Other serine protease inhibitors are believed to prevent goblet hyperplasia and metaplasia which is induced by elastase in chronic bronchitis.

Among the corticosteroids which may be used in the present invention are triamcinolone acetonide, flurandrenolide, prednisone, amcinonide, beclometasone valerate, dexamethasone, betamethasone valerate, halocinonide, clocortolone, hydrocortisone valerate, and the like.

Beclomethasone valerate is particularly useful because it inhibits goblet cell hyperplasia. Also, it inhibits anti-IgE-induced histamine release from basophils although not from mast cells.

The serine protease inhibitors which are contemplated in the present invention are any of the inhibitors, their analogs, derivatives or salts of the human type which can inhibit mast cells or bind with any one or more of the protease derived from eosinophils, basophils and/or neutrophils such as elastase, cathepsin-G, tryptase, chymase, kinins, kallikrein, tumor necrosis factor, chymotrypsin, GEF, collagenase, inhibit IgE production and the like.

The serine protease inhibitors included in the present invention are human alpha 1-antichymotrypsin, alpha 1-antitrypsin, alpha 2-macroglobulin, eglin, elastinal 1, elastin 3, eglin 2, C-reactive protein, beta 1-antigellagenase, serine amyloid A protein, alpha cysteine protease inhibitors, inter-alpha-trypsin inhibitor, secretory leucocyte protease inhibitor, bronchial mucous inhibitor, and C-1-inhibitor. The inhibitors of the invention may be natural or prepared by recombinant means. The recombinant may be glycosylated.

The use of alpha 1-antitrypsin and alpha 1-antichymotrypsin in combination with a corticosteroid has been especially useful in the treatment of the various inflammatory pulmonary conditions including those which are induced by autoimmune disease, virus and bacterial infections.

The inhibitors of the invention may be derived from human blood or prepared by cloning, by conventional techniques utilizing an oligonucleotide probe or antibody probe, and the like. The recombinant gene product of the invention is especially useful since it is free of contaminating viruses when produced.

The analogs, salts and derivatives may be formed utilizing conventional techniques associated with other proteins without effecting the utility of the compound. There may be prepared the alkali metal salts, acid-addition salts, and esters similar to other proteins or peptides.

The compositions of the invention are preferably administered to patients showing an increase in IgE through a patch or serum test. That is, the patient shows a positive allergic condition. These allergic patients having asthma respond quickly to therapy with the serine protease when administered by inhalation form.

The present invention also provides a method for the prophylactic and direct treatment of patients suffering from asthma and the symptoms thereof. In accordance with the invention, there is administered to the patient an effective amount of the corticosteroid and a microcrystalline serine protease inhibitor, its analog, derivative or salt in a nebulizer.

The following examples further illustrate the practice of this invention, but are not intended to be limiting thereof. It will be appreciated that the selection of actual amounts of specific serine protease inhibitors and corticosteroids to be administered to any individual patient (human or animal) will fall within the discretion of the attending physician and will be prescribed in a manner commensurate with the appropriate dosages will depend on the stage of the disease and like factors uniquely within the purview of the attending physician.

EXAMPLE I

Equal amounts of microcrystalline alpha-1-antitrypsin and dexamethasone are suspended in oleic acid and added into a metering aerosol canister together with trichloromonofluoromethane and dichlorodifluoromethane so that the unit has a molecular proportion of alpha-1-antitrypsindexamethasone to the propellant between 3:1 and 3:2. The unit delivers a quantity of drug equivalent to 42 mcg. The composition can be used in the treatment of asthma.

EXAMPLE II

Microcrystalline alpha-1-antitrypsin and alpha-1-antitrypsin and beclometasone valerate are suspended in oleic acid and added into a metering aerosol canister together with trichloromonofluoramethane and dichlorodifluoromethane so that the unit has a molecular proportion of drug to the propellant between 1 and 3:2.

EXAMPLE III

A composition for use with a nebulizer for treating bronchitis is prepared from the following ingredients.

| Ingredient | % wt |
|---|---|
| $\alpha_1$-antichymotrypsin | 0.1 |
| $\alpha_1$-antitrypsin | 0.1 |
| 10% saline solution | 99.7 |
| dexamethasone | 0.1 |

The composition is nebulized using a AQUAVENT nebulizer (mallinckrodt).

The serine protease inhibitor may be provided using PROLASTIN (Cutter Biological) which comprises a combination of the two inhibitors.

We claim:

1. A method for the prophylaxis or direct treatment of mast cell implicated pulmonary disease in mammals which comprises administering by inhalation a composition of a synergistically effective amount of a corticosteroid and a natural or recombinant alpha 1-antitrypsin which inhibits the degranulation of mast cells and/or has an affinity to basophils, the mediators of mast cells or T-cells.

2. The method of claim 1 wherein said mast cell implicated pulmonary disease is asthma.

3. The method of claim 1 wherein said disease is bronchitis.

4. The method of claim 1 wherein said mediators comprise neutrophils, basophils and eosinophils.

5. The method of claim 1 wherein said mediators comprise cathepsin G and elastase.

6. The method of claim 1 wherein said corticosteriod is selected from the group consisting of triamcinolone acetonide, fluroandrenolide, prednisone, beclomethasone valerate, amcinolone, dexamethasone, betamethasone valerate, halocinonide, clocortolone and hydrocortisone valerate.

7. The method of claim 1 wherein said composition is non-aqueous.

8. A pharmaceutical composition for treatment of a patient suffering from a mast cell implicated pulmonary disease comprising the combination of an effective amount of a natural or recombinant alpha 1-antitrypsin which inhibits the degranulation of mast cells and/or has an affinity to basophils, the mediators of mast cells or T-cells, a synergistically effective amount of a corticosteroid, and a pharmaceutically acceptable carrier suitable for administration to the patient by inhalation therapy.

9. The composition of claim 8 wherein said corticosteroid is selected from the group consisting of triamcinolone acetonide, fluroandrenolide, prednisone, beclomethasone valerate, amcinolone, dexamethasone, betamethasone valerate, halocinonide, clocortolone and hydrocortisone valerate.

10. The composition of claim 8 which is non-aqueous.

* * * * *